United States Patent [19]

Thevignot

[11] Patent Number: 5,149,812
[45] Date of Patent: Sep. 22, 1992

[54] INDUSTRIAL PROCESS FOR THE PREPARATION OF (1S)-1-[N-(4-O-DEACETYL-23-VINBLAS-TINOYL)AMINO]-2-METHYLPROPYL DIETHYL PHOSPHONATE AND ITS SALTS

[75] Inventor: Roger Thevignot, Bolbec, France

[73] Assignee: Adir et Compagnie, Courbevoie, France

[21] Appl. No.: 674,653

[22] Filed: Mar. 25, 1991

[30] Foreign Application Priority Data

Jan. 31, 1991 [FR] France .................. 91 01073

[51] Int. Cl.⁵ .................. C07F 9/65; C07F 9/576; C07F 9/59
[52] U.S. Cl. .................. 546/23
[58] Field of Search .................. 546/23

[56] References Cited

FOREIGN PATENT DOCUMENTS 0346235 12/1989 European Pat. Off. .............. 546/23

OTHER PUBLICATIONS

Chemical Abstracts, vol. 113(11) Abstract No. 113:91020-x Sep. 10, 1990.
Chemical Abstracts, vol. 112(25) abst. No. 112:235,666s Jun. 18, 1990.
Anticancer Research 10: 139–144 (1990).
The Journal of Medicinal Chemistry, 34, No. 7, (1991), pp. 1998–1999.

Primary Examiner—Alan L. Rotman
Attorney, Agent, or Firm—Gordon W. Hueschen

[57] ABSTRACT

Industrial synthesis of (1S)-1-[N-(4-O-deacetyl-23-vinblastinoyl)amino]-2-methylpropyl diethyl phosphonate and its salts by condensation of 4-O-deacetylvinblastinoic acid (obtained by alkaline hydrolysis of vinblastine sulphate) with phosamine (+) (dextrorotatory isomer of 1-amino-2-methylpropyl diethyl phosphonate), by means of BOP, a peptide coupling reagent, [1-benzotriazolyloxytris(dimethylamino)phosphonium hexafluorophosphonate]; and, if desired, the product obtained is converted into a salt with suitable acids.

4 Claims, No Drawings

INDUSTRIAL PROCESS FOR THE PREPARATION OF (1S)-1-[N-(4-O-DEACETYL-23-VINBLASTINOYL-)AMINO]-2-METHYLPROPYL DIETHYL PHOSPHONATE AND ITS SALTS

The present invention relates to a new industrial process for the preparation of (1S)-1-[N-(4-O-deacetyl-23-vinblastinoyl)amino]-2-methylpropyl diethyl phosphonate and its salts.

(1S)-1-[N-(4-O-deacetyl-23-vinblastinoyl)amino]-2-methylpropyl diethyl phosphonate and its salts, which are described in the European Patent Application published under No. 0318392, have very valuable pharmacological properties which enable them to be used therapeutically, in particular in the treatment of neoplasic disorders in living beings.

As regards the process for the preparation of that ester and its salts, the prior art is illustrated by European Patent Application No. 0318392, which describes a process which consists in reacting an excess of anhydrous hydrazine with a methanolic solution of vinblastine base to give N-(4-O-deacetyl-23-vinblastinoyl)hydrazide, which is converted, by means of sodium nitrite, in an acidic medium, into 3-demethoxycarbonyl-4-O-deacetylvinblastine-3-carboxazide, which is reacted with 1-amino-2-methylpropyl diethyl phosphonate to give 1-[N-(4-O-deacetyl-23-vinblastinoyl)amino]-2-methylpropyl diethyl phosphonate, which can be purified by chromatography and, if desired, converted into a salt with a suitable acid in an ethanolic medium.

Such a process results in a yield that is relatively poor (not greater than 30%) and is, especially, difficult to exploit industrially on account of the use of anhydrous hydrazine, which is dangerous to handle, and of the instability of the azide intermediate formed during the synthesis.

For that reason, as well as because of the therapeutic value of the product, the Applicant has carried out investigations, the result of which is the subject of the present invention.

The present invention relates therefore to an industrial process for the preparation of (1S)-1-[N-(4-O-deacetyl-23-vinblastinoyl)amino]-2-methylpropyl diethyl phosphonate of the formula I:

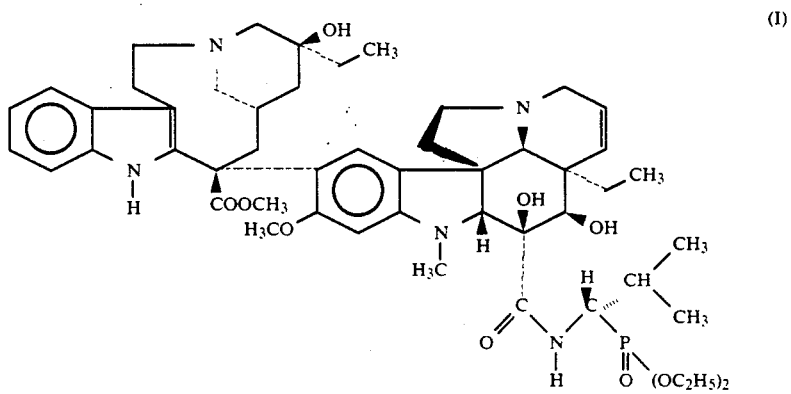

characterised in that:
4-O-deacetylvinblastinoic acid of the formula II:

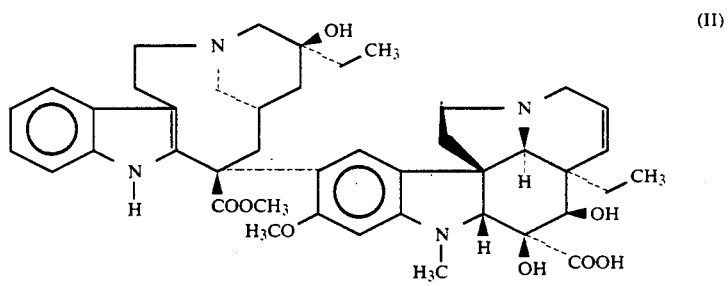

is condensed with the dextrorotatory isomer of phosamine or 1-amino-2-methylpropyl diethyl phosphonate of the formula III:

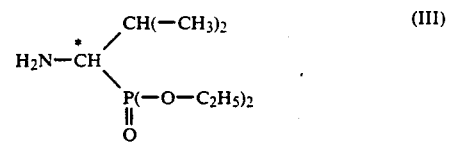

by means of the peptide coupling reagent BOP or 1-benzotriazolyloxy-tris(dimethylamino)phosphonium hexafluorophosphate;

and, if desired, the product obtained is purified by preparative chromatography on silica and then converted into addition salts with suitable acids.

It is especially advantageous to carry out the condensation of compounds II and III by means of the coupling reagent BOP in the presence of triethylamine and in tetrahydrofuran.

The 4-O-deacetylvinblastinoic acid (II) used as starting material was prepared by alkaline hydrolysis of vinblastine sulphate. Phosamine, the starting material of the formula III, is a known product [cf. Synthesis (1981), 57].

In comparison with the process described in European Patent Application No. 0318392, the process of the present invention has important advantages, especially as regards quality, industrial implementation and safety.

The absence of by-products in the present process results in a better quality of the reaction medium and increased quality of the final product, the purity of which is greater than 98%, whereas it did not exceed 95% with the previous process.

The present synthesis is carried out in two steps, instead of three as in the previous process, starting from vinblastine (base or sulphate, as appropriate). The yield is very much greater than that obtained with the previous process (60% instead of 25-30%).

The stability, safety and reproducibility which the conventional process lacks on account of the instability of the azide intermediate are achieved in the present process, in which the absence of a dangerous product to be handled (anhydrous hydrazine) also increases safety.

The following Examples illustrate the present invention, but do not limit it.

EXAMPLE 1

Preparation of (1S)-1-[N-(4-O-deacetyl-23-vinblastinoyl)amino]-2-methylpropyl diethyl phosphonate a) Preparation of 4-O-deacetylvinblastinoic acid: 10 g ($10.78 \times 10^{-3}$ moles) of 98% vinblastine sulphate are suspended in 60 ml of pure synthesis methanol. The suspension is stirred and purged with argon, and 15 ml of a 4N sodium hydroxide solution are poured in over a period of 5 minutes. The whole is stirred at 25°±5° C. for 72 hours protected from light, and then acidified to a pH of approximately 5 by the addition of approximately 1 ml of acetic acid.

The methanol is removed in vacuo and the concentrate is taken up in 100 ml of water and 50 ml of methylene chloride.

After neutralisation to pH 7.2 by the addition of sodium hydrogen carbonate, the acid precipitates.

The whole is cooled in ice for one hour, filtered and washed with ice-water, and the filtered product is dried at 25° C, in vacuo in the presence of phosphoric anhydride.

In this manner, 6.90 g of amorphous 4-O-deacetylvinblastinoic acid, titrating 95% (HPLC) are obtained (in a yield of 80%).

b) Preparation of (1S)-1-[N-(4-O-deacetyl-23-vinblastinoyl)amino]-2-methylpropyl diethyl phosphonate: 6.64 g ($8.35 \times 10^{-3}$ moles) of 4-O-deacetylvinblastinoic acid, prepared previously, are suspended and stirred under argon in 46.5 ml of anhydrous tetrahydrofuran dried on molecular sieves. The suspension is cooled to from 0 to −2° C., and there are then added 1.075 g ($10.64 \times 10^{-3}$ moles) of triethylamine, 2.23 g ($10.65 \times 10^{-3}$ moles) of the dextrorotatory isomer of 1-amino-2-methylpropyl diethyl phosphonate [or phosamine(+)] and, over a period of 15 minutes, in portions, 4.71 g ($10.64 \times 10^{-3}$ moles) of Fluka BOP reagent [or 1-benzotriazolyloxy-tris(dimethylamino)-phosphonium hexafluorophosphate].

The mixture is stirred vigorously until everything has dissolved (which takes approximately 7 hours) and then is left to stand at 0° C. for 67 hours. The tetrahydrofuran is then removed in vacuo and the residue is taken up in 500 ml of methylene chloride and washed in succession with 100 ml of water, 100 ml of a normal solution of hydrochloric acid, 50 ml of an aqueous 7% sodium hydrogen carbonate solution and finally with 200 ml of water.

The methylene chloride is then removed in vacuo. In this manner, 8.24 g of (1S)-1-[N-(4-O-deacetyl-23-vinblastinoyl)amino]-2-methylpropyl diethyl phosphonate, titrating 80% (HPLC), are obtained (in a yield of 83%).

The product so obtained may be purified by preparative chromatography on a Jobin Yvon stainless steel column which is charged with:

2 kg of Merck RP silica, 18.25–40 μ, 60 Å

15 g of crude (1S)-1-[N-(4-O-deacetyl-23-vinblastinoyl)amino]-2-methylpropyl diethyl phosphonate (80% HPLC) and 100 litres of eluant formed by methanol-disodium phosphate (70–30).

The eluate fractions containing the purified product are evaporated in vacuo. The concentrate is extracted with $8 \times 250$ ml of methylene chloride, and the extracts are dried by removal in vacuo of the methylene chloride.

The residue is dissolved in 50 ml of methylene chloride and the solution is clarified on a 0.5 μ millipore filter and then evaporated to dryness again. In this manner there are obtained (in a yield of 58%) 7.33 g of purified (1S)-1-[N-(4-O-deacetyl-23-vinblastinoyl)amino]-2-methylpropyl diethyl phosphonate in the form of a yellowish-white amorphous powder titrating 97–98% (HPLC).

EXAMPLE 2

Preparation of (1S)-1-[N-(4-O-deacetyl-23-vinblastinoyl)-amino]-2-methylpropyl diethyl phosphonate sulphate:

5.36 g ($5.38 \times 10^{-3}$ moles) of purified (1S)-1-[N-(4-O-deacetyl-23-vinblastinoyl)amino]-2-methylpropyl diethyl phosphonate are dissolved at ambient temperature in 20.75 g ($5.66 \times 10^{-3}$ moles) of sulphuric ethanol (0.273 mole/kg); (the solution of sulphuric ethanol being prepared by the addition of a mixture of 3.2 ml of concentrated $H_2SO_4$ d: 1.83, and 5 ml of water to ethanol qs 250 ml, the solution is then titrated and used as and when required).

The solution is filtered on 0.5 μ millipore and washed with 6 ml of ethanol, and then the solution is poured onto 900 ml of methyl tert.-butyl ether.

After standing for 2 hours, the precipitate that has formed is filtered, washed with $3 \times 10$ ml of methyl tert.-butyl ether and then dried in vacuo at 20° C. In this manner, 5.25 g of (1S)-1-[N-(4-O-deacetyl-23-vinblastinoyl)amino]-2-methylpropyl diethyl phosphonate sulphate are obtained in the form of a yellowish-white powder titrating 98% (HPLC).

I claim:

1. Process for the preparation of (1S)-1-[N-(4-O-deacetyl-23-vinblastinoyl)amino-2-methylpropyl diethyl phosphonate of the formula I:

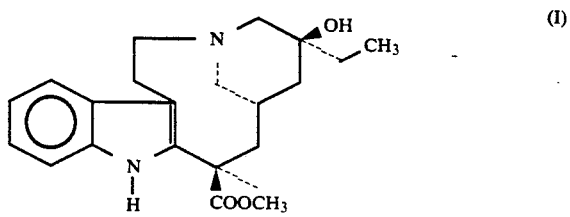

-continued

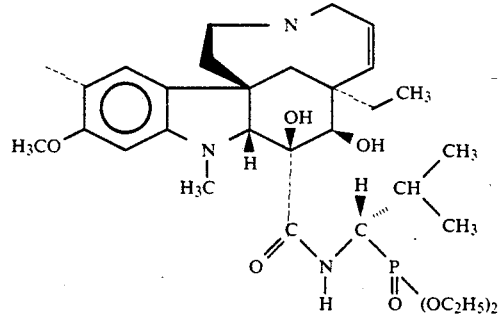

or a salt thereof, wherein:

4-O-deacetylvinblastinoic acid of the formula II:

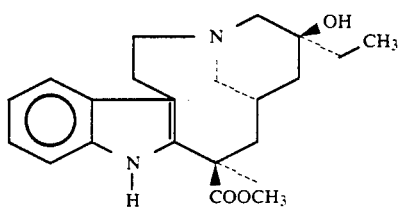

-continued

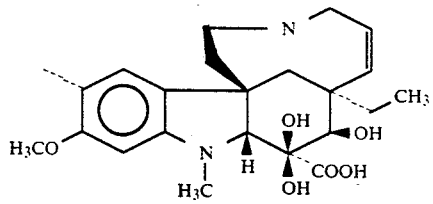

is condensed with the dextrorotatory isomer of phosamine or 1-amino-2-methylpropyl diethyl phosphonate of the formula III:

$$H_2N-\overset{*}{C}H \begin{array}{c} CH(-CH_3)_2 \\ P(-O-C_2H_5)_2 \\ \parallel \\ O \end{array} \quad (III)$$

by means of the functional precursor peptide coupling reagent BOP or 1-benzotriazolyloxy-tris(-dimethylamino)phosphonium hexafluorophosphate in a solvent comprising tetrahydrofuran; and, if desired, the product obtained is purified by preparative chromatography on silica and then converted into an addition salt with an acid.

2. Process according to claim 1, wherein the condensation of compounds II and III with employment of the coupling reagent BOP is carried out in the presence of triethylamine in a tetrahydrofuran medium.

3. Process according to claim 1, wherein the 4-O-deacetylvinblastinoic acid (II) starting material is prepared by alkaline hydrolysis of vinblastine sulphate.

4. Process according to claim 1, wherein the (1S)-1-[N-(4-O-deacetyl-23-vinblastinoyl)amino]-2-methylpropyl diethyl phosphonate of formula (I) is converted into a salt by employment of sulphuric acid in ethanol to give (1S)-1-[N-(4-O-deacetyl-23-vinblastinoyl)amino]-2-methylpropyl diethyl phosphonate sulphate.

* * * * *

UNITED STATES PATENT AND TRADEMARK OFFICE
CERTIFICATE OF CORRECTION

PATENT NO. : 5,149,812

DATED : Sep. 22, 1992

INVENTOR(S) : Roger Thevignot

It is certified that error appears in the above-identified patent and that said Letters Patent is hereby corrected as shown below:

Column 1, line 5; move the closing parenthesis ")" from the beginning of line 5 to the end of line 4 and insert before the hyphen " - ".

Column 4, approximately line 26; move the closing parenthesis from the beginning of line 26 and insert at the end of line 25 before the hyphen " - ".

Column 5, the top center portion of this continuation of formula (I):

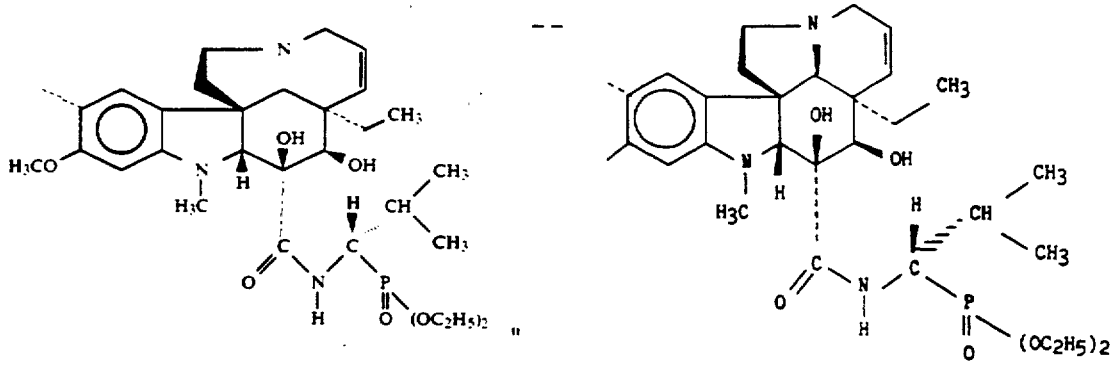

UNITED STATES PATENT AND TRADEMARK OFFICE
CERTIFICATE OF CORRECTION

PATENT NO.  : 5,149,812
DATED       : Sep. 22, 1992
INVENTOR(S) : Roger Thevignot It is certified that error appears in the above-identified patent and that said Letters Patent is hereby corrected as shown below:

Column 6, the top center portion of this continuation of formula (II):

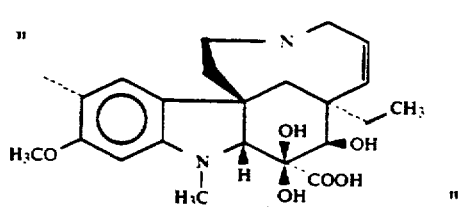 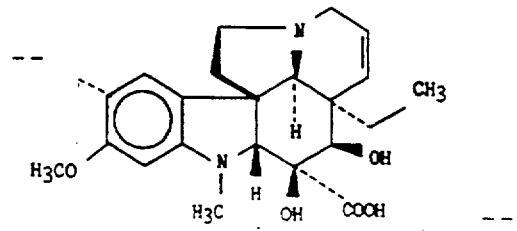

Column 6, line 21; "by means" should read -- with employment --.
(PA 3-19-91, P. 1)

Signed and Sealed this

Twelfth Day of October, 1993

Attest:

BRUCE LEHMAN

Attesting Officer    Commissioner of Patents and Trademarks